(12) United States Patent
Trifonov et al.

(10) Patent No.: US 11,931,393 B2
(45) Date of Patent: Mar. 19, 2024

(54) BIOLOGICALLY ACTIVE FOOD ADDITIVE FOR NORMALIZING THE FUNCTION OF THE THYROID GLAND

(71) Applicant: Parapharm LLC, Penza (RU)

(72) Inventors: Vyacheslav N Trifonov, Penza region (RU); Yulia A. Elistratova, Penza (RU); Konstantin G. Elistratov, Penza (RU); Natalia V. Kurus', Penza (RU)

(73) Assignee: Parapharm LLC, Penza (RU)

( * ) Notice: Subject to any disclaimer, the term of this patent is extended or adjusted under 35 U.S.C. 154(b) by 445 days.

(21) Appl. No.: 15/430,600

(22) Filed: Feb. 13, 2017

(65) Prior Publication Data
US 2017/0151301 A1  Jun. 1, 2017

Related U.S. Application Data

(63) Continuation-in-part of application No. 14/238,322, filed as application No. PCT/RU2012/000269 on Apr. 10, 2012, now abandoned.

(51) Int. Cl.
*A61K 36/73* (2006.01)
*A23L 33/105* (2016.01)
*A61K 36/03* (2006.01)
*A61K 36/28* (2006.01)

(52) U.S. Cl.
CPC ............ *A61K 36/73* (2013.01); *A23L 33/105* (2016.08); *A61K 36/03* (2013.01); *A61K 36/28* (2013.01); *A23V 2002/00* (2013.01)

(58) Field of Classification Search
CPC ........ A61K 36/73; A61K 36/78; A61K 36/02; A61K 36/03
USPC .................... 424/737, 195.17, 725
See application file for complete search history.

(56) References Cited

U.S. PATENT DOCUMENTS

| | | | | |
|---|---|---|---|---|
| 6,342,208 B1 * | 1/2002 | Hyldgaard | ............... | A61K 8/06 424/400 |
| 2002/0192245 A1 * | 12/2002 | Jensen | ...................... | A61K 8/97 424/401 |
| 2003/0152652 A1 * | 8/2003 | Baker | ..................... | A61K 36/28 424/737 |
| 2007/0110731 A1 * | 5/2007 | Riley | .................... | A61K 31/728 424/93.7 |
| 2007/0299046 A1 * | 12/2007 | Brooks | ................ | C07D 487/22 514/185 |
| 2009/0011041 A1 * | 1/2009 | Musaeva | ................ | A61K 31/56 424/520 |
| 2010/0292193 A1 * | 11/2010 | McBride | .............. | A61K 31/407 514/152 |
| 2011/0105623 A1 * | 5/2011 | Benjamin | .............. | A61K 31/10 514/711 |

FOREIGN PATENT DOCUMENTS

| | | | |
|---|---|---|---|
| RU | 2203676 C2 * | 5/2003 | |
| RU | 2351354 C1 * | 4/2009 | |
| RU | 2351354 C1 * | 4/2009 | |
| RU | 2375924 C1 * | 12/2009 | |

* cited by examiner

*Primary Examiner* — Aaron J Kosar
*Assistant Examiner* — Jacob A Boeckelman
(74) *Attorney, Agent, or Firm* — Patentagar PLLC; Alexander Rabinovich

(57) ABSTRACT

A biologically active food additive for normalizing the function of the thyroid gland comprises roots or rhizome or the above-ground part of white cinquefoil, or a mixture thereof, purple echinacca and laminaria, with the following ratio of components in mass %: 10-75 of white cinquefoil, 10-50 of purple echinacea and 10-80 of laminaria. The technical result of the invention is the showing of increased efficacy in treating thyroid gland disorders and enhancing the body's immune status, with no side of effects.

5 Claims, No Drawings

BIOLOGICALLY ACTIVE FOOD ADDITIVE FOR NORMALIZING THE FUNCTION OF THE THYROID GLAND

CROSS-REFERENCE TO RELATED APPLICATIONS

This application is a continuation-in-part of the U.S. application Ser. No. 14/238,322 filed Feb. 11, 2014, pending, which is a U.S. National phase application of the International application PCT/RU2012/000269, filed Apr. 10, 2012, the entire content of the both applications being incorporated into the present application by reference.

BACKGROUND OF THE DISCLOSURE

1. Field of Technology

This disclosure relates to a food processing industry, specifically to food supplements (biologically active dietary additives (BAA)) for the normalization of thyroid functions.

2. Description of related art

A prior art search on this matter uncovered patent RU2333764, published 2008 Sep. 20, for "Medication for the treatment and prevention of the disease of thyroid gland", the medication comprising roots and rhizomes of white cinquefoil (*Potentilla alba* L.), herb of bur beggar-ticks (*Bidens tripartite* L.) and roots of common licorice (*Glycyrrhiza glabra* L.). As the process of treating the thyroid gland is lengthy and usually takes months, the use of common licorice does not seem desirable. The herb is known to possess antiandrogenic effect suppressing the testosterone production, with all undesirable effects that it may imply—androgen deficiency, impotence, and advanced development of osteoporosis because of insufficient anabolic action of testosterone on bone tissue—just to name a few.

Also known is Russian patent RU2351354, published 2009 Apr. 10, for "Medication for the treatment and prevention of the disease of thyroid gland". The medication is a tea mix comprising white cinquefoil, roots of common licorice, herb of bur beggar-ticks and thallomes of Laminaria saccharina (*Laminaria*), with the following component ratio—20:5:8:7, respectively, the white cinquefoil being present in the form of roots, rhizomes or herb or a mixture thereof, the forms of the medication including ground herb powder, alcohol-water tincture, liquid and dry extractions. The drawbacks of having licorice in the above-discussed composition are applicable to this tea mix as well.

Known in the art is also a method of causing a hematinic effect in an animal or a human, comprising administering a composition comprising Echinacea (*Echinacea*) (U.S. application 2003/0152652, published 2003 Aug. 14). The hematinic effect is understood to be mainly related to preventing and/or treating a hematological disorder, which in turn is associated with various anemias, anemia of hypothyroidism including. It is believed that the composition fails in treating hypothyroidism itself. It can help to raise hemoglobin—but only as long as Echinacea is administered.

The applicants are not aware of a means for the effective normalization of the thyroid function, even though it is much needed.

BRIEF SUMMARY

The general object of the disclosure is widening the range of biologically active dietary additives (BAA), possessing a wide spectrum effect on the human body and contributing to the health improvement of the population. Particularly, the disclosure is directed to a BAA for the effective normalizing of the function of the thyroid gland. This problem is solved in the present proposal by providing a BAA comprising white cinquefoil (*Potentilla alba*) in the form of roots or rhizomes or herb thereof, or their mixture, as well as purple coneflower (*Echinacea purpurea*) and Laminaria (*Laminaria*), with the following ratio of the components in mass percent %: white cinquefoil—10-75, purple coneflower—10-50, Laminaria—10-80.

The technical result of the BAA is providing a biologically active composition with higher bioavailability, that has optimally selected component ratio and shows no side effects, to thus allow using it in the most effective way for the prevention of diseases of the thyroid gland and the raise of body immunological status.

DETAILED DESCRIPTION

Thyroid disorders are accompanied by an immunity decrease. Therefore, it was suggested to intensify the therapeutic effect of the white cinquefoil by the action of *Echinacea purpurea*. For that reason, "Parapharm" LLC, Penza, Russia, offers to release biologically active additive formula, sold under the tradename TIREO-VIT. "TIREO-VIT" comprises purple coneflower (*Echinacea purpurea*), laminaria and white cinquefoil, which contains a significant quantity of macro- and microelements, shows antibacterial activity, normalizes the thyroid function, and is used for the prevention of such thyroid disorders as thyrotoxicosis, hyperthyroidism, hyperplasia and hypothyroidism. There are two effective agents (active principles) in the composition: elemental iodine and anion of iodous acid that is contained in the root of a white cinquefoil (laminaria contains iodine in the form of iodine organic compounds and iodides), as well as polysaccharides of coneflower that have an immunopotentiating activity.

The BAA is recommended for the use as an effective biologically active dietary additive in the case of different thyroid disorders such as: hypothyroidism (hypofunction), hyperthyroidism (hyperfunction, thyrotoxicosis, Basedow-Graves, DTG (diffuse toxic goiter) disease), autoimmune thyroiditis (Hashimoto thyroiditis, CAT), euthyroid goiter (diffusive, nodular/multinodular), hyperplasia of thyroid gland.

Additional properties of medicinal plants that the "TIREO-VIT" comprises are as follows: white cinquefoil contains carbohydrates (starch), iridoids, saponins, phenol-carbonic acids, flavonoids (quercetine) and tanning agents. The unique value of the plant is that in terms of micro- and macroelements it contains quite significant number of elements from the Periodic Table of Elements. While using white cinquefoil, a mineral balance and salt exchange within the body turn to normal, a hormonal balance straightens, and metabolic processes normalize. All agents contained in cinquefoil are not toxic and have no side effects on the body.

Specifically, flavonoids (remedies comprising vitamin P) have a positive impact on the blood vessel walls, regulating their ductance, eliminating their brittleness and fragility; they reduce heart rate and increase their amplitude, reduce arterial tension, have effect on the blood count by stimulating the production of erythrocytes and leukocytes and reducing the level of cholesterol; they also intensify a bile flow and increase the tone of intestinal canal.

Further, phenolcarbonic acids (pyrocatechins, hydroquinones and pyrogallols) have a broad capacity for a reversible oxidation with the formation of semiquinone radicals and quinones, thereby they easily react with thiol groups of proteins; particularly, their influence on vascular and cellular permeability might be explained by the cooperation of these agents with proteins of cellular membranes and vassal-tissue barriers.

Yet further, iridoids-phytochemicals provide a therapeutic effect in case of thyroid gland disorders. It has been proved that iridoids kill very harmful free radicals, maintain normal level of cholesterol, increase energy, stimulate cardiac performance, reinforce immune system, guard the body against various kinds of inflammations, keep the cells away from mutation, and increase healthy activity of the brain.

White cinquefoil is a reservoir of Mn, Zn, Cu, Se, Co, Fe, Si, Al. It demonstrates antibacterial activity, and for that reason it is applied in case of colitis, enterocolitis, dysentery, diarrhea, gastrointestinal torminas as astringent and hemostatic remedy. Besides that, herbalists recommend to use white cinquefoil for preventive treatment of liver diseases, disorders in cardiovascular system and gastrointestinal tract, particularly ulcer, as well as an antiseptic and wound-healing remedy. White cinquefoil is used in cases of gout and rheumatism, it is also a good blood cleaner. White cinquefoil is a reliable remedy in the case of ovarian dysfunction, descent of womb and dysmenorrhea. The intake of white cinquefoil regulates arterial blood pressure; normalizes a body weight; regulates calcium metabolism to thereby improve the condition of skin, hair and nails. It contributes to the resolution of soft tumors, nodular lumps; it has been proved that white cinquefoil contributes to the excretion of radiation, resolves cysts and myomas.

*Echinacea purpurea* contains essential oils, glycosides, amides, antibiotic polyacetylenes, inulin, B-group vitamins, iron that is needed to form red cells, calcium needed for strong bones and teeth, selenium for the capacity to resist diseases, as well as silicium that is needed to form tissues. Echinacea is used in case of disorders associated with the reduction of the functional status of immune system induced by chronic inflammatory diseases, exposure to ionizing radiation, ultraviolet rays, chemotherapeutic compounds and long-term antibiotic therapy. In some metabolic disorders (diabetes and hepatic disorders), influence of various chemical compounds of toxic nature (such as heavy metals, pesticides, insecticides and fungicides) contained in the air and food substances, the intake of Echinacea-containing preparations stimulates the immune system. Additionally, Echinacea preparations have antibacterial, anti-viral and anti-mycotic properties. Echinacea preparations inhibit the growth and reproduction of streptococcus, staphylococcus, Escherichia coli, viruses of influenza, herpes, stomatitis; they are effective in cases of inflammatory diseases (rheumatism, polyarthritis, prostatitis and gynecological disorders), upper air passages diseases, in various wound processes (trophic ulcers and central osteitis) and microbial eczema.

Laminaria (sea girdle) contains iodine (around 3%) in the form of iodine-organic compounds and iodides; vitamins A, B1, B2, B12, C, and O, folic acid, carbohydrates (polysaccharide laminarin, mannitol, alginic acid), aging pigment, sodium, calcium, magnesium, copper, and cobalt, bromine salts, traces of arsenic, salts of potassium. Due to the great content of iodine and vitamins, it is used in a form of powder for the treatment and prophylaxis of atherosclerosis and goiter.

In oncological clinic, it has been uncovered that the powder of laminaria contributes to the improvement of a general state of the patients and frame of their mind (Kovalyova N. G. Treating by plants, Medicine, Moscow, 1972, p. 153). It is also recommended in case of chronic constipations as eccoprotic (2-3 g of powder for 150 ml of water, nocte), as well as for the improvement of metabolic process and in the case of gout. In China and Japan, laminaria is used in treatment and prophylaxis of the thyroid disorders.

It was found that hypothyroidism has a strong impact on immune resistance, especially in children. It turns out that particularly affected are Immunoglobulins A (IgA) responsible for humoral immunity. The low level of IgA can be life-threatening, and, being in a critical condition, the body does not have enough resources to respond properly to a thyroid gland correction by white cinquefoil. Therefore, a decision to combine administration of white cinquefoil, laminaria, and Echinacea proved highly reasonable. Increasing the level of IgA in patients with thyroid disorders helps normalize the thyroid gland much faster. Specifically regarding white cinquefoil and Echinacea, both plants increase energy, and they are immune response modifiers, activators of cell-mediated immunity and intrinsic cellular metabolism. However, their combined use unexpectedly and significantly intensifies recited pharmacological effects. A research conducted at the applicant's request showed that the immunity enhancement in response to Echinacea with white cinquefoil is substantially more pronounced than where Echinacea is used by itself. Particularly, the maximum activity of Echinacea appears strictly subjected to availability of bioflavonoids which are contained in white cinquefoil. Incorporation of laminaria into the proposed composition is motivated by the fact that it is rich with organic iodine needed to achieve the maximum of therapeutic effect, especially in case of hypothyroidism and euthyroid goiter. Another research demonstrated that when the proposed composition of white cinquefoil, Echinacea and laminaria is used, the effect of stabilizing the thyroid gland function was even more pronounced as compared to the use of substantially higher dosage of white cinquefoil only. The combined use of the specified plants in thyroid function disorders is not known in the art.

It has been found in the course of numerous experiments that to receive an additive with the supreme bioavailability of all included components, as well as for the purpose of obtaining the maximum efficacy of this additive in respect of prevention of thyroid gland disorders and enhancing the immunological status of the body, the following ratio of the compounds (in mass percent (%)) has to be maintained: white cinquefoil (roots and rhizomes or the herb, or their mixture)—10-75, *Echinacea purpurea* 10-50, laminaria 10-80. The ranges were selected by recognizing that the lower range limits cut off areas of inefficiency whereas the upper range limits cut off the areas where the safety of the composition can be compromised. The BAA can be produced in a powdered, tableted or capsular form, as well as in the form of aqueous alcoholic extract and forms made based on this extract, more specifically: powder, tablets or capsules.

The preparation is illustrated with the following nonlimiting example:

To prepare BAA, the ingredients are combined in the following ratio: 50 mg of milled roots of white cinquefoil, 10 mg of milled herb of *Echinacea purpurea*, and 10 mg of milled thallomes of laminaria. The ingredients are thoroughly mixed, and tablets are made of the resultant mixture.

BAA prepared in accordance with the above example was used in testing on 10 volunteers: pregnant women who during a prior examination were first diagnosed with hypothyroidism, nodules of thyroid gland and compromised immunity. For the period of pregnancy, the women were taking BAA in accordance with the example thrice daily. The pregnancy of all women proceeded with no complications, and delivery went with no complications as well. Results of the analyses after 6 months intake of BAA in accordance with the example demonstrated that this BAA has led the thyroid gland to the euthyroid state, and the immunity improved substantially. The use of the BAA induced no side effects on pregnant women.

Same successful results have been obtained after testing the BAA with food, where other quantitative ratios of the components were chosen within the selected ranges.

Thus, the disclosed BAA owing to the properly selected qualitative and quantitative ratio of the components provides effective prophylactic of thyroid gland disorders and raises the immunological status without any side effects.

Summing up, the proposed combination of white cinquefoil, Echinacea and laminaria in the composition significantly enhances the effectiveness of the normalization of the thyroid gland function. Particularly, comparative trials showed that thyreostatic effect with the use of the proposed composition was achieved in nearly half the time required for the prior art composition without Echinacea. An additional important advantage of the composition over the prior art is the absence of allergic response thereto. Thus, though the composition comprises natural ingredients, their combined use therein results in obtaining characteristics which are markedly different from what was achieved when the ingredients of the proposed composition were used separately or in other combinations. Therefore, the above-discussed synergistic effect resulting from the combination of the components in the composition is "a new and useful end" (see *Funk Brothers Seed Col. V. Kalo Inoculant Col.*—333 U.S. 130 (1948)—"He who discovers a hitherto unknown phenomenon of nature has no claim to a monopoly of it which the law recognizes. If there is to be invention from such a discovery, it must come from the application of the law of nature to a new and useful end."). It is believed therefore that in conformity with the USPTO IEG the proposed composition is a patent eligible subject matter.

It is also believed that the teachings from the prior art do not make the proposed composition obvious. First, because the prediction of properties of a new combination of ingredients is not evident. It can be self-evident in hindsight. There are numerous examples of poor results in mixing components despite each of them is characterized positively. Second, because there has been a long-standing need in an effective means for normalizing the function of the thyroid gland, and this need was left unsatisfied, the notoriety of all the ingredients of the proposed composition notwithstanding. Third, because a simple combination of the prior art publications would not make the proposed composition, since some ingredients in the prior art, the presence of which would deteriorate the properties of the resulting composition, should be omitted, and this whole task would be well beyond the capacity that can be expected from a skilled artisan. Fourth, because "[o]bviousness cannot be established by combining the teachings of the prior art to produce the claimed invention, absent some teachings or suggestion supporting the combination" (*ACP Hosp. Sys., Inc. v. Montefiore Hosp.*, 732 F.2d 1572, 1577, 221 USPQ 929, 933 (Fed. Cir. 1984), and neither of the prior art publications teaches or suggests such a combination.

The invention claimed is:

1. A biologically active food additive for normalizing the function of the thyroid gland, the additive being made in a tablet or capsular form and comprising 10-75 wt % white cinquefoil (*Potentilla alba*), 10-50 wt % purple echinacea (*Echinacea purpurea*), and 10-80 wt % laminaria (*Laminaria*), whereby a health-promoting effect at least in cases of hypothyroidism, hyperthyroidism, and autoimmune thyroiditis is achieved through an increase in IgA levels.

2. The biologically active food additive as claimed in claim 1, wherein white cinquefoil includes roots thereof.

3. The biologically active food additive as claimed in claim 1, wherein white cinquefoil includes rhizomes thereof.

4. The biologically active food additive as claimed in claim 1, wherein white cinquefoil includes an herb thereof.

5. The biologically active food additive as claimed in claim 1, wherein white cinquefoil includes a mixture of roots, rhizomes and herb thereof.

* * * * *